United States Patent
Kobayashi et al.

(10) Patent No.: US 6,486,218 B2
(45) Date of Patent: Nov. 26, 2002

(54) METHOD OF MANUFACTURING METHANOL

(75) Inventors: Kazuto Kobayashi, Tokyo (JP); Masaki Iijima, Tokyo (JP); Kazuhiro Morita, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 09/931,095

(22) Filed: Aug. 17, 2001

(65) Prior Publication Data

US 2002/0040067 A1 Apr. 4, 2002

(30) Foreign Application Priority Data

Aug. 21, 2000 (JP) ........................................ 2000-249670

(51) Int. Cl.[7] .............................................. C07C 27/00
(52) U.S. Cl. ........................ 518/700; 518/702; 518/704
(58) Field of Search ................................. 518/700, 702, 518/704

(56) References Cited

U.S. PATENT DOCUMENTS 6,218,439 B1 * 4/2001 Kobayashi et al. ......... 518/713

FOREIGN PATENT DOCUMENTS

EP 0650950 * 10/1994

* cited by examiner

Primary Examiner—Jafar Parsa
(74) Attorney, Agent, or Firm—Oblon, Spivak, McClelland, Maier & Neustadt, P.C.

(57) ABSTRACT

A natural gas having steam and carbon dioxide added thereto is supplied into a reaction tube of a reformer provided with the reaction tube and a combustion radiation section for heating the reaction tube by combustion of a fuel so as to carry out a reaction between the hydrocarbon contained in the natural gas and the steam added to the natural gas, thereby forming a synthetic gas containing hydrogen, carbon monoxide and carbon dioxide. Then, the synthetic gas is subjected to a reaction in the presence of a methanol synthesizing catalyst. A crude methanol obtained is subjected to a gas-liquid separation. Further, a liquid crude methanol separated in the separation is distilled. In the particular methanol manufacturing process, a part of the purge gas obtained in the separation is recycled into the natural gas having steam and carbon dioxide added thereto in advance.

4 Claims, 2 Drawing Sheets

METHOD OF MANUFACTURING METHANOL

CROSS-REFERENCE TO RELATED APPLICATIONS

This application is based upon and claims the benefit of priority from the prior Japanese Patent Application No. 2000-249670 filed Aug. 21, 2000, the entire contents of which are incorporated herein by reference.

BACKGROUND OF THE INVENTION

1. Field of the Invention

The present invention relates to a method of manufacturing methanol.

2. Description of the Related Art

The conventional method of manufacturing methanol ($CH_3OH$) is as follows:

Synthetic Gas Forming Process

Natural gas having steam and carbon dioxide added thereto is supplied into a reaction tube of a reformer, the reformer being provided with the reaction tube loaded with, for example, a nickel-based catalyst, and a combustion radiation section for heating the reaction tube by the combustion of a fuel. In this case, the hydrocarbon in the natural gas reacts with the steam so as to generate a synthetic gas containing as main components hydrogen, carbon monoxide and carbon dioxide.

Since the steam reforming reaction described above is an endothermic reaction, the fuel is combusted in the fuel combustion section so as to heat the reaction tube.

Crude Methanol Synthetic Process

The synthetic gas contained hydrogen, carbon monoxide and carbon dioxide is reacted in the presence of a methanol synthetic catalyst under a predetermined pressure and a predetermined temperature so as to synthesize a crude methanol.

Recovery Process of Liquid Crude Methanol

The crude methanol is subjected to a gas-liquid separation for separation into a liquid crude methanol and a purge gas mainly containing hydrogen. The separated purge gas is recycled into the combustion radiation section so as to be utilized as a part of the fuel.

Distillation Process

The liquid crude methanol recovered in the recovery process is distilled in one or a plurality of distillation towers so as to separate the crude methanol into a refined methanol and a waste water containing an organic compound having a boiling point lower than that of methanol (hereinafter referred to as a "low boiling point organic compound"), an organic acid, and an organic compound having a boiling point higher than that of methanol (hereinafter referred to as a "high boiling point organic compound").

Methanol is manufactured through the processes described above.

BRIEF SUMMARY OF THE INVENTION

An object of the present invention is to provide a method of manufacturing methanol, in which a purge gas obtained by a gas-liquid separation of a crude methanol and mainly containing hydrogen is recycled to a natural gas having steam and carbon dioxide added thereto so as to utilize the purge gas as a part of the fuel, thereby increasing the methanol yield.

According to a first aspect of the present invention, there is provided a method of manufacturing methanol, comprising:

a synthetic gas forming step, in which a natural gas having steam and carbon dioxide added thereto is supplied into a reaction tube of a reformer provided with the reaction tube and a combustion radiation section for heating the reaction tube by the combustion of a fuel so as to bring about a reaction between the hydrocarbon contained in the natural gas and the steam, thereby forming a synthetic gas containing mainly hydrogen, carbon monoxide and carbon dioxide;

a crude methanol synthetic step for performing the reaction of the synthetic gas in the presence of a methanol synthetic catalyst so as to synthesize a crude methanol;

a gas-liquid separation step for separating the crude methanol into a liquid crude methanol and a purge gas mainly containing hydrogen; and a distillation step for distilling the liquid crude methanol so as to separate a refined methanol;

wherein a part of the purge gas is recycled into the natural gas having steam and carbon dioxide added thereto in advance.

In the method of manufacturing methanol according to the present invention, it is desirable for a part or all of the carbon dioxide gas added to the natural gas to be the carbon dioxide recovered from at least one of the combustion waste gas generated from the combustion radiation section of the reformer and the combustion waste gas generated from the boiler for the steam generation.

In the method of manufacturing methanol according to the present invention, it is acceptable for a part of the purge gas to be recycled into the combustion radiation section of the reformer so as to be utilized as a part of the fuel.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

The method of the present invention for manufacturing methanol will now be described in detail with reference to the accompanying drawings.

Figure 1:
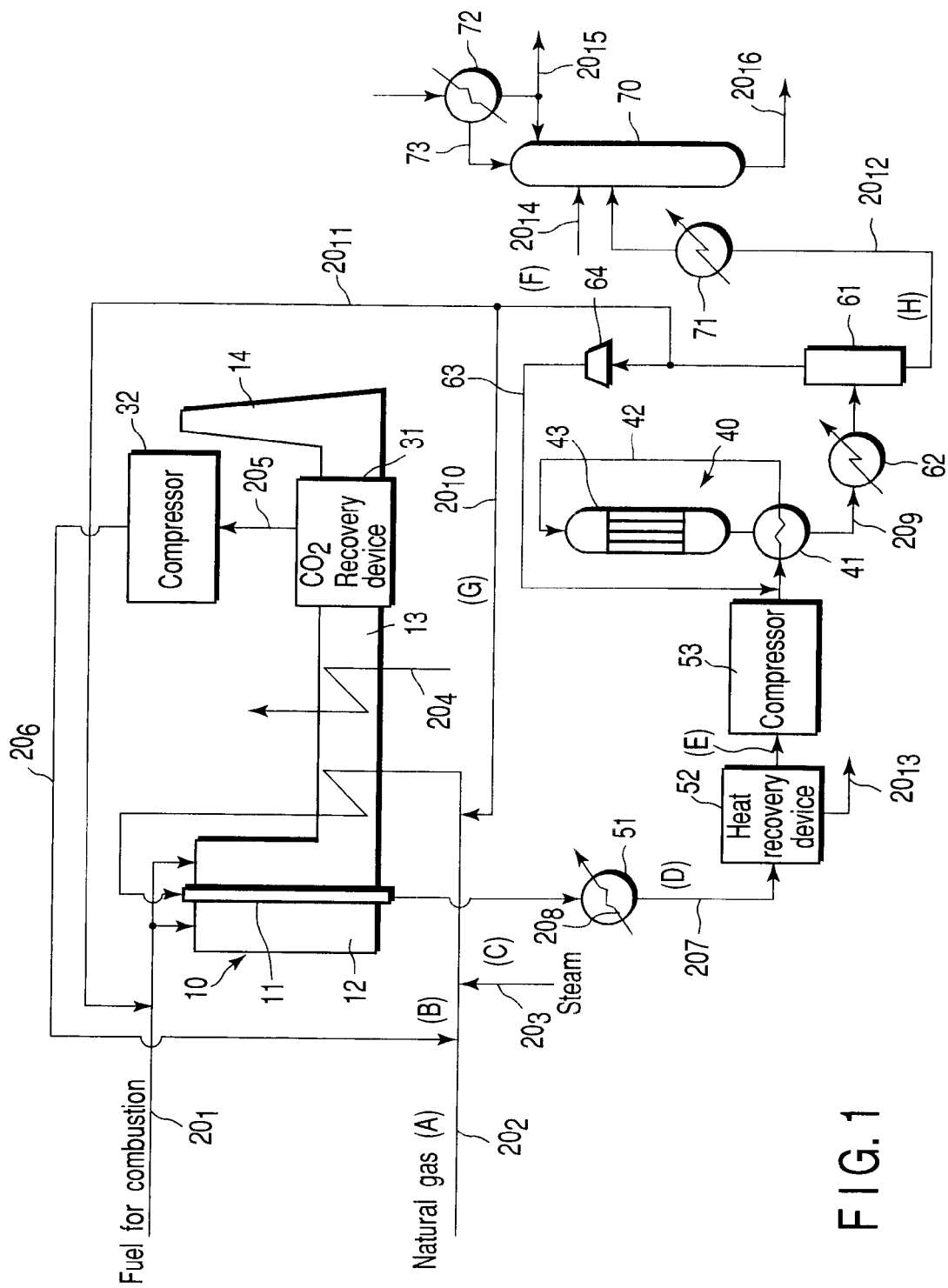
FIG. 1 is a diagram schematically exemplifying a methanol manufacturing plant according to one embodiment of the present invention.

FIG. 1 is a diagram schematically showing the gist portion of a plant used for the method of the present invention for manufacturing methanol.

As shown in the drawing, the methanol manufacturing plant comprises a reformer 10 including a steam reforming reaction tube 11, a combustion radiation section 12 arranged to surround the reaction tube 11 for heating the reaction tube 11 by combusting a fuel, and a smokestack 14 communicating with the combustion radiation section 12 through a convection section (waste heat recovery section) 13. A catalyst, e.g., a nickel-based catalyst, is loaded in the reaction tube 11. A fuel introducing fluid passageway $20_1$ is connected to the combustion radiation section 12 of the reformer 10.

A raw material gas introducing fluid passageway $20_2$ is connected to the upper end of the reaction tube 11 through the convection section 13 of the reformer 10. It is possible to mount a desulfurizer (not shown) to the fluid passageway $20_2$. A steam introducing fluid passageway $20_3$ is connected to the raw material gas introducing fluid passageway $20_2$ upstream of the convection section 13. Further, a fluid passageway $20_4$ for circulating, for example, a boiler water extends to cross the convection section 13 of the reformer 10 such that a heat exchange is performed between the combustion waste gas of the convection section 13 and the boiler water circulated within the fluid passageway $20_4$ so as to cool the combustion waste gas and, at the same time, to heat the boiler water itself, thereby generating a high pressure steam.

A carbon dioxide recovery device 31 is arranged in the convection section 13 of the reformer 10 so as to recover carbon dioxide in the combustion waste gas generated from the convection section 13. The carbon dioxide recovery device 31 is connected to a compressor 32 via a fluid passageway $20_5$. Further, the compressor 32 is connected to the raw material gas introducing fluid passageway $20_2$ upstream of the reformer 10.

A methanol synthesizing reaction apparatus 40 is arranged downstream of the reformer 10 and is connected to the reaction tube 11 of the reformer 10 via a fluid passageway $20_7$. The reaction apparatus 40 comprises a pre-heater 41 and a methanol synthesizing reactor 43 to which is supplied the synthesized gas from the pre-heater 41 through a circulating fluid passageway 42. A methanol synthesizing catalyst is loaded in the reactor 43. A heat exchanger 51, a heat recovery device 52 and a compressor 53 are mounted to the fluid passageway $20_7$ interposed between the reformer 10 and the pre-heater 41 in the order mentioned as viewed from the reformer 10. A fluid passageway $20_8$ crosses the heat exchanger 51 so as to heat, for example, the boiler water circulated through the fluid passageway $20_8$, thereby generating a high pressure steam.

The reactor 43 of the methanol synthesizing apparatus 40 is connected to a gas-liquid separator 61 through a fluid passageway $20_9$. The pre-heater 41 and a cooler 62 are mounted to the fluid passageway $20_9$. The gas-liquid separator 61 is connected to the fluid passageway $20_7$ upstream of the pre-heater 41 through a gas circulating fluid passageway 63. A gas compressor 64 is mounted to the gas circulating fluid passageway 63. A purge gas fluid passageway $20_{10}$ is branched from that portion of the gas circulating fluid passageway 63 which is interposed between the gas-liquid separator 61 and the gas compressor 64 so as to be connected to the raw material gas introducing fluid passageway $20_2$. Also, the purge gas fluid passageway $20_{10}$ is branched to form a branched purge gas fluid passageway $20_{11}$, which is connected to the fuel introducing fluid passageway $20_1$.

The gas-liquid separator 61 is connected to a distillation tower 70 through a fluid passageway $20_{12}$. A liquid crude methanol pre-heater 71 is mounted to the fluid passageway $20_{12}$. Further, a condenser 72 is connected to the top region of the distillation tower 70 through a circulating passageway 73.

How to manufacture methanol will now be described with reference to the manufacturing plant shown in FIG. 1.
(1) Synthesizing Gas Forming Step In the first step, a fuel for combustion is supplied into the combustion radiation section 12 of the reformer 10 through the fuel introducing fluid passageway $20_1$ for the combustion in the presence of the air so as to heat the inside of the reaction tube 11 to a sufficiently high temperature, e.g., 850 to 900° C. The reaction tube 11 is heated because the reforming reaction carried out within the reformer 10 is an endothermic reaction. The combustion waste gas containing carbon dioxide generated in the combustion radiation section 12 flows through the convection section 13 to reach the smokestack 14. While passing through the convection section 13, the combustion waste gas carries out a heat exchange with a natural gas having steam added thereto and circulated within the raw material gas introducing fluid passageway $20_2$ and with the boiler water circulated through the fluid passageway $20_4$. Carbon dioxide contained in the cooled combustion waste gas is recovered in the carbon dioxide recovery device 31 so as to be supplied into the compressor 32 through the fluid passageway $20_5$. The combustion waste gas having carbon dioxide removed therefrom is discharged to the air atmosphere through the smokestack 14.

The natural gas containing methane as a main component is supplied into the raw material gas introducing fluid passageway $20_2$. In this case, a predetermined amount of carbon dioxide compressed by the compressor 32 is added to the natural gas through the fluid passageway $20_6$. Also, a predetermined amount of steam is added to the natural gas, to which carbon dioxide has been added, through the steam introducing fluid passageway $20_3$. It is possible to utilize the steam generated by the heat exchange between the boiler water and the synthetic gas, which is carried out in the heat exchanger 51, and by the heat exchange between the boiler water and the combustion waste gas, which is carried out in the convection section 13 of the reformer 10. Further, a predetermined amount of the unreacted gas referred to herein later, which mainly contains hydrogen, is added as a purge gas to the natural gas having carbon dioxide and steam added thereto.

In adding carbon dioxide and steam to the natural gas, it is desirable for the molar ratio of methane ($CH_4$) contained in the natural gas to steam ($H_2O$) to fall within a range of between 1:1.5 and 1:5, and for the molar ratio of methane contained in the natural gas to carbon dioxide ($CO_2$) to fall within a range of between 1:1 and 1:3.

The natural gas having carbon dioxide and steam added thereto is circulated through the raw material gas introducing fluid passageway $20_2$ and is preheated when passing through the convection section 13 of the reformer 10. Further, the natural gas is heated to a sufficiently high temperature and, then, introduced into the reaction tube 11.

The natural gas containing methane ($CH_4$) as a main component and having steam and carbon dioxide added thereto, which is supplied into the reaction tube 11 of the reformer 10, is subjected to a steam reformation within the reaction tube 11 in the presence of a catalyst. As a result, methane is mainly subjected to a steam reformation so as to generate a synthetic gas containing hydrogen, carbon monoxide and carbon dioxide, as denoted by reaction formulas (1) and (2) given below:

$$CH_4 + H_2O \rightleftharpoons CO + 3H_2 \quad (1)$$

$$CO + H_2O \rightleftharpoons CO_2 + H_2 \quad (2)$$

As is apparent from reaction formulas (1) and (2) given above, 4 mols of hydrogen and 1 mol of carbon dioxide are generated by the reaction between 1 mol of methane and 2 mols of steam. In the actual reaction system, however, obtained is a composition close to the chemical reaction equilibrium composition determined by the temperature and pressure at the outlet of the reaction tube 11.

(2) Crude Methanol Synthesizing Step

The synthetic gas formed in the reformer 10 is supplied into the heat exchanger 51 through the fluid passageway 20₇. In the heat exchanger 51, the boiler water passing through the fluid passageway 20₈ is heated so as to generate a high pressure steam. At the same time, the synthetic gas itself is cooled and, then, supplied to the heat recovery device 52 so as to be cooled to room temperature. In this case, the steam contained in the synthetic gas is condensed, and the condensed water is taken out through a fluid passageway 20₁₃ so as to be utilized as, for example, a process water.

The synthetic gas having the condensed water separated therefrom is supplied to the compressor 53 through the fluid passageway 20₇ so as to be compressed to have a pressure adapted for the methanol synthesizing reaction, e.g., 50 to 150 atms. The compressed synthetic gas is further supplied to the pre-heater 41 of the reaction apparatus 40 for synthesizing methanol through the fluid passageway 20₇. In the pre-heater 41, the compressed synthetic gas is preheated to a temperature adapted for the methanol synthesizing reaction, e.g., 200 to 300° C., and, then, further supplied into the reactor 43 loaded with a methanol synthesizing catalyst through the circulating fluid passageway 42. Incidentally, the unreacted gas, which is separated in the gas-liquid separator 61 referred to herein later, is supplied to the fluid passageway 20₇ upstream of the pre-heater 41 through the gas circulating fluid passageway 63 so as to be mixed with the synthetic gas. Reactions (3) and (4) given below are carried out in the reactor 43 so as to form a composition containing the synthesized methanol:

$$CO + 2H_2 \rightleftharpoons CH_3OH \quad (3)$$

$$CO_2 + 3H_2 \rightleftharpoons CH_3OH + 2H_2O \quad (4)$$

Impurities such as dimethyl ether and ethanol are also formed by side reactions. These impurities are also contained in the liquid crude methanol together with methanol formed by the reactions given above.

A catalyst such as a copper-based catalyst is used as the methanol synthesizing catalyst. Particularly, it is desirable for the methanol synthesizing catalyst to consist of oxides containing Cu, Zn, Al, Ga and M, M being at least one element selected from the group consisting of alkaline earth metal elements and rare earth elements, the oxides having a high durability under an atmosphere containing a high concentration of carbon dioxide, and the atomic ratio of Cu:Zn:Al M being 100:10 to 200:1 to 20:0.1 to 20.

Recovery Step of Liquid Crude Methanol

The reaction mixture formed in the reactor 43 is supplied into the pre-heater 41 and, then, into the cooler 62 successively through the fluid passageway 20₉ so as to be cooled to substantially room temperature. In this case, methanol and water contained in the reaction mixture are condensed substantially completely so as to form a liquid crude methanol flowing into the gas-liquid separator 61. In the gas-liquid separator 61, the reaction mixture is separated into the liquid crude methanol and the unreacted gas mainly containing hydrogen.

The unreacted gas is transferred into the gas compressor 64 through the gas circulating fluid passageway 63. After being compressed in the gas compressor 64, the unreacted gas is circulated into the fluid passageway 20₇ upstream of the pre-heater 41 through the gas circulating fluid passageway 63 so as to be supplied into the reactor 43 together with the synthetic gas. A part of the unreacted gas is supplied as a purge gas into the raw material gas introducing fluid passageway 20₂ through the purge gas fluid passageway 20₁₀ so as to be utilized as a part of the raw materials. Also, the remaining unreacted gas is supplied as a purge gas into the fuel introducing fluid passageway 201 through the branched purge gas fluid passageway 20₁₁ so as to be utilized as a part of the fuel in the combustion radiation section of the reformer 10.

Distillation Process

The crude methanol separated in the gas-liquid separator 61 is supplied to the distillation tower 70 through the crude methanol pre-heater 71 mounted to the fluid passageway 20₁₂. Also, a small amount of water is supplied to the distillation tower 70 through the fluid passageway 20₁₄. In the distillation tower 70, the liquid crude methanol is separated under the function of the condenser 72 into a refined methanol having a high purity and a waste water containing the low boiling point organic compound and the high boiling point organic compound formed as by-products. The refined methanol is withdrawn as a product to the outside through a fluid passageway 20₁₅. On the other hand, the waste water is discharged to the outside through a fluid passageway 20₁₆.

Incidentally, carbon dioxide added to the natural gas is not limited to that recovered from the combustion waste gas formed in the combustion radiation section. It is also possible to utilize carbon dioxide gas recovered from the combustion waste gas generated in, for example, the boiler and discarded in, for example, another factory. In other words, carbon dioxide generated from, for example, other factories, which was discarded in the past, can be effectively utilized as a raw material in the method of the present invention for manufacturing methanol so as to decrease the amount of carbon dioxide discharged to the air atmosphere. In other words, the method of the present invention is effective for suppressing global warming, which is a serious environmental problem nowadays.

A single distillation tower is used in the embodiment described above. However, it is possible to use a plurality of distillation towers.

As described above, in the method of the present invention, the purge gas mainly containing hydrogen, which is obtained by the gas-liquid separation of the crude methanol, is partly recycled into the natural gas having steam and carbon dioxide added thereto so as to utilize the purge gas as a part of the raw material. In the conventional method, however, the purge gas is recycled into the combustion radiation section of the reformer so as to utilize the purge gas as a part of the fuel. It follows that the method of the present invention permits forming a synthetic gas containing higher molar ratios of CO and H₂ in the forming process of the synthetic gas, compared with the conventional method. It follows that the method of the present invention permits increasing the crude methanol production and the refined methanol production.

It should also be noted that carbon dioxide recovered from the combustion waste gas generated from the combustion radiation section of the reformer (or the combustion waste gas generated from the boiler) can be utilized in the present invention so as to decrease the amount of carbon dioxide discharged to the outside in the methanol manufacturing process. It follows that the methanol manufacturing plant can be made economical in the case where the tax on the carbon dioxide gas discharge is introduced and where the carbon dioxide gas discharge is regulated.

A preferred embodiment of the present invention will now be described with reference to the methanol manufacturing plant shown in FIG. 1.

Example 1

A fuel, e.g., a natural gas, was introduced into the combustion radiation section 12 of the reformer 10 at a flow rate of 540 kmol/hr so as to be combusted in the combustion radiation section 12 in the presence of the air. Also, a natural gas, steam and carbon dioxide recovered from the combustion waste gas of the reformer 10 and from the synthetic gas were supplied into the raw material gas introducing fluid passageway $20_2$ under the conditions shown in Table 1 so as to carry out the steam reformation in the reaction tube 11 of the reformer 10, the crude methanol formation in the reaction apparatus 40 for synthesizing methanol, the recovery of the liquid crude methanol in the gas-liquid separator 61, and the recycle of the purge gas into the raw material gas line, thereby manufacturing methanol. Table 1 also shows the composition of the methanol thus manufactured.

Item (A) shown in Table 1 denotes the natural gas supplied to the raw material gas introducing fluid passageway $20_2$. Item (B) represents the carbon dioxide gas recovered in the carbon dioxide recovery device 31 from the combustion waste gas generated from the combustion radiation section 12 of the reformer 10 and compressed by the compressor 32 so as to be supplied to the raw material gas introducing fluid passageway $20_2$. Item (C) represents steam supplied to the raw material gas introducing fluid passageway $20_2$. Item (D) represents the synthetic gas supplied to the heat recovery device 52 through the heat exchanger 51. Item (E) represents the synthetic gas supplied from the heat recovery device 52 into the compressor 53. Item (F) represents the unreacted gas (purge gas) separated in the gas-liquid separator 61. Item (G) represents a part of the purge gas separated in the gas-liquid separator 61 so as to be recycled into the raw material gas introducing fluid passageway $20_2$. Further, item (H) shown in Table 1 represents the liquid crude methanol separated in the gas-liquid separator 61. Incidentally, these items (A) to (H) are shown in FIG. 1.

Comparative Example 1

Figure 2:
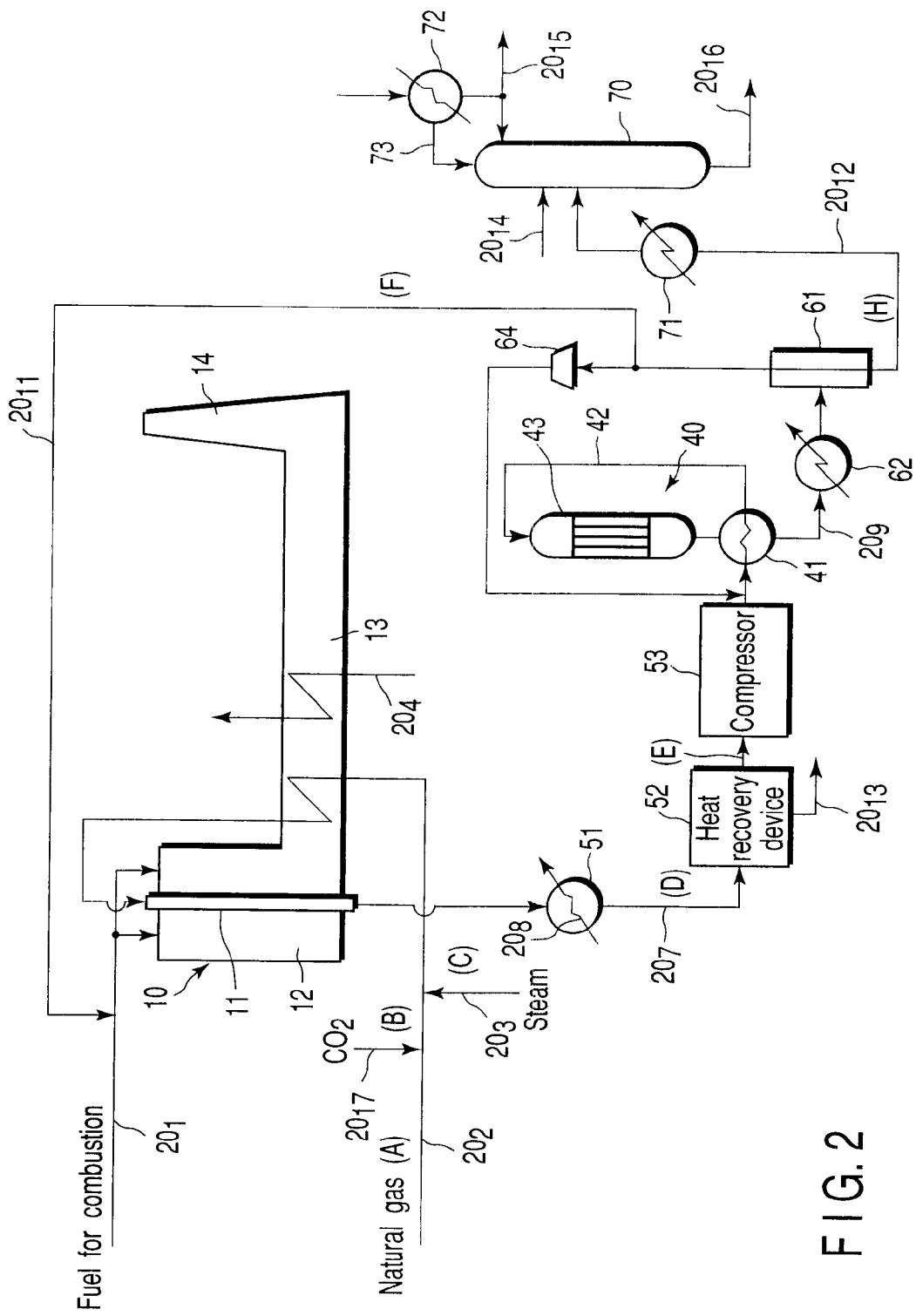
FIG. 2 is a diagram schematically exemplifying a methanol manufacturing plant for the comparative case.

Methanol was manufactured as in Example 1, except that used was a methanol manufacturing plant shown in FIG. 2. In this case, a carbon dioxide gas manufactured outside the plant was added to the natural gas through a fluid passageway $20_{17}$, and the unreacted gas (purge gas) separated from the gas-liquid separator 61 was recycled to the fuel introducing fluid passageway $20_1$ so as to be utilized as a fuel of the combustion radiation section 12 of the reformer 10. Table 2 shows the composition of the methanol thus obtained.

Item (A) shown in Table 2 represents the natural gas supplied into the raw material gas introducing fluid passageway $20_2$. Item (B) represents the carbon dioxide gas supplied to the raw material gas introducing fluid passageway $20_2$. Item (C) represents steam supplied into the raw material gas introducing fluid passageway $20_2$. Item (D) represents the synthetic gas supplied to the heat recovery device 52 through the heat exchanger 51. Item (E) represents the synthetic gas supplied from the heat recovery device 52 into the compressor 53. Item (F) represents a part of the purge gas separated in the gas-liquid separator 61 so as to be recycled into the fuel introducing fluid passageway $20_1$. Further, item (G) represents the liquid crude methanol separated in the gas-liquid separator 61. Incidentally, these items (A) to (G) are also shown in Table 2.

TABLE 1

(Example 1)

| Item | (A) | (B) | (C) | (D) | (E) | (F) | (G) | (H) |
|---|---|---|---|---|---|---|---|---|
| Composition | | | | | | | | |
| $CH_4$ (mol %) | 94 | — | — | 3.9 | 5.2 | 12.3 | 12.3 | 0.6 |
| $C_2H_6$ (mol %) | 6 | — | — | — | — | — | — | — |
| $H_2$ (mol %) | — | — | — | 56.4 | 75.1 | 84.2 | 84.2 | 0.3 |
| CO (mol %) | — | — | — | 10.5 | 14.0 | 1.3 | 1.3 | — |
| $CO_2$ (mol %) | — | 100 | — | 3.9 | 5.2 | 1.6 | 1.6 | 0.4 |
| $H_2O$ (mol %) | — | — | 100 | 25.3 | 0.5 | — | — | 20.1 |
| $CH_3OH$ (mol %) | — | — | — | — | — | 0.6 | 0.6 | 78.6 |
| Total (mol%) | 100 | 100 | 100 | 100 | 100 | 100 | 100 | 100 |
| Flow rate (kg · mol/hr) | 1000 | 250 | 3446 | 9388 | 7053 | 2911 | 2620 | 1589 |

TABLE 2

(Comparative Example 1)

| Item | (A) | (B) | (C) | (D) | (E) | (F) | (G) |
|---|---|---|---|---|---|---|---|
| Composition | | | | | | | |
| $CH_4$ (mol %) | 94 | — | — | 1.9 | 2.9 | 25.1 | 1.1 |
| $C_2H_6$ (mol %) | 6 | — | — | — | — | — | — |
| $H_2$ (mol %) | — | — | — | 46.5 | 68.7 | 66.8 | 0.2 |
| CO (mol %) | — | — | — | 12.0 | 17.7 | 1.7 | — |
| $CO_2$ (mol %) | — | 100 | — | 6.9 | 10.2 | 5.8 | 1.4 |
| $H_2O$ (mol %) | — | — | 100 | 32.7 | 0.5 | — | 25.1 |
| $CH_3OH$ (mol %) | — | — | — | — | — | 0.6 | 72.2 |
| Total (mol %) | 100 | 100 | 100 | 100 | 100 | 100 | 100 |
| Flow rate (kg · mol/hr) | 1000 | 250 | 3180 | 6305 | 4268 | 422 | 1566 |

To reiterate, a part of the purge gas separated in the gas-liquid separator 61 is recycled in the method of the present invention (Example 1) into the raw material gas introducing fluid passageway $20_2$ so as to be added to the natural gas having carbon dioxide and steam added thereto in advance. In Comparative Example 1, however, a part of the purge gas separated in the gas-liquid separator 61 is recycled as a fuel gas into the fuel gas introducing fluid passageway 20₁. As is apparent from Tables 1 and 2, Example 1 permits increasing the methanol production, compared with Comparative Example 1.

As described above, the present invention provides a method of manufacturing methanol, in which a purge gas mainly containing hydrogen, which is obtained by the gas-liquid separation from the crude methanol, is recycled so as to be added to the natural gas having steam and carbon dioxide added thereto in advance, thereby utilizing the purge gas as a part of the raw material. It follows that the methanol manufacturing method of the present invention permits increasing the methanol production.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing methanol comprising:

supplying a natural gas having steam and carbon dioxide added thereto into a reaction tube of a reformer provided with said reaction tube and a combustion radiation section, heating the reaction tube by the combustion of a fuel to react the hydrocarbon contained in said natural gas and said steam, thereby forming a synthetic gas containing mainly hydrogen, carbon monoxide and carbon dioxide;

reacting said synthetic gas in the presence of a methanol synthetic catalyst to synthesize a crude methanol;

separating said crude methanol into a liquid crude methanol and a purge gas mainly containing hydrogen; and distilling said liquid crude methanol so as to separate a refined methanol;

wherein a part of said purge gas is recycled into said natural gas having said steam and said carbon dioxide added thereto.

2. The method of manufacturing methanol according to claim 1, wherein a part of all of said carbon dioxide added to said natural gas comprises a carbon dioxide gas recovered from at least one of the combustion waste gas generated from the combustion radiation section of said reformer and the combustion waste gas generated from a boiler for generating steam.

3. The method of manufacturing methanol according to claim 1, wherein said carbon dioxide and said steam are added to said natural gas such that the molar ratio of methane ($CH_4$) contained in said natural gas to said steam ($H_2O$) falls within a range of between 1:1.5 and 1:5, and the molar ratio of methane ($CH_4$) contained in said natural gas to said carbon dioxide gas ($CO_2$) falls within a range of between 1:1 and 1:3.

4. The method of manufacturing methanol according to claim 1, wherein a part of said purge gas is recycled to said combustion radiation section of said reformer so as to be utilized as a part of the fuel.

* * * * *